US005175069A

United States Patent [19]

Shuttleworth et al.

[11] Patent Number: 5,175,069

[45] Date of Patent: Dec. 29, 1992

[54] MALEIMIDE BLUE DYES FOR COLOR FILTER ARRAY ELEMENT

[75] Inventors: Leslie Shuttleworth; Helmut Weber, both of Webster, N.Y.

[73] Assignee: Eastman Kodak Company, Rochester, N.Y.

[21] Appl. No.: 716,568

[22] Filed: Jun. 14, 1991

[51] Int. Cl.[5] .......................... G03C 7/06; D06P 5/00; C07D 207/244

[52] U.S. Cl. ........................................ 430/7; 430/201; 430/237; 430/964; 430/517; 503/227; 548/548; 8/471

[58] Field of Search .................. 430/201, 964, 7, 517; 503/227; 8/471, 634; 548/548

[56] References Cited

U.S. PATENT DOCUMENTS

| | | | |
|---|---|---|---|
| 3,096,339 | 7/1963 | Martin | 260/310 |
| 5,079,214 | 1/1992 | Long et al. | 430/201 |

Primary Examiner—Richard L. Schilling
Attorney, Agent, or Firm—Harold E. Cole

[57] ABSTRACT

A thermally-transferred color filter array element comprising a support having thereon a polymeric dye image-receiving layer containing a thermally-transferred image comprising a repeating pattern of colorants of a maleimide blue dye having the formula:

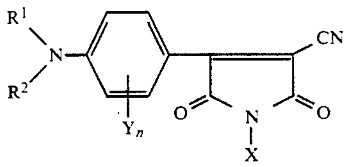

wherein:

$R^1$ and $R^2$ each independently represents hydrogen; a substituted or unsubstituted alkyl group having from 1 to about 8 carbon atoms; a cycloalkyl group having from about 5 to about 8 carbon atoms; or a substituted or unsubstituted alkenyl group having from about 2 to about 8 carbon atoms;

$R^1$ and $R^2$ may represent the elements which may be taken together to form a 5- or 6-membered heterocyclic ring;

each Y independently represents hydrogen; a substituted or unsubstituted alkyl group having from 1 to about 8 carbon atoms; an alkoxy group $OR^1$; halogen; or two adjacent Y's may represent the atoms which may be taken together to form a fused aromatic ring;

n is 0 to 4;

the position of Y ortho to the nitrogen may also be combined with $R^1$ to form a 5- or 6-membered non-aromatic, single or double nitrogen-containing, heterocyclic ring, thus forming a fused ring system; and X is $R^1$; a substituted or unsubstituted acyl group having from 2 to about 9 carbon atoms; a substituted or unsubstituted aroyl group having from about 7 to about 18 carbon atoms; or a substituted or unsubstituted heteroaroyl group having from about 2 to about 10 carbon atoms.

20 Claims, No Drawings

MALEIMIDE BLUE DYES FOR COLOR FILTER ARRAY ELEMENT

This invention relates to the use of a maleimide blue dye for a thermally-transferred color filter array element which is used in various applications such as a liquid crystal display device.

In recent years, thermal transfer systems have been developed to obtain prints from pictures which have been generated electronically from a color video camera. According to one way of obtaining such prints, an electronic picture is first subjected to color separation by color filters. The respective color-separated images are then converted into electrical signals. These signals are then operated on to produce cyan, magenta and yellow electrical signals. These signals are then transmitted to a thermal printer. To obtain the print, a cyan, magenta or yellow dye-donor element is placed face-to-face with a dye-receiving element. The two are then inserted between a thermal printing head and a platen roller. A line-type thermal printing head is used to apply heat from the back of the dye-donor sheet. The thermal printing head has many heating elements and is heated up sequentially in response to the cyan, magenta and yellow signals. The process is then repeated for the other two colors. A color hard copy is thus obtained which corresponds to the original picture viewed on a screen. Further details of this process and an apparatus for carrying it out are contained in U.S. Pat. No. 4,621,271 by Brownstein entitled "Apparatus and Method For Controlling A Thermal Printer Apparatus," issued Nov. 4, 1986, the disclosure of which is hereby incorporated by reference.

Another way to thermally obtain a print using the electronic signals described above is to use a laser instead of a thermal printing head. In such a system, the donor sheet includes a material which strongly absorbs at the wavelength of the laser. When the donor is irradiated, this absorbing material converts light energy to thermal energy and transfers the heat to the dye in the immediate vicinity, thereby heating the dye to its vaporization temperature for transfer to the receiver. The absorbing material may be present in a layer beneath the dye and/or it may be admixed with the dye. The laser beam is modulated by electronic signals which are representative of the shape and color of the original image, so that each dye is heated to cause volatilization only in those areas in which its presence is required on the receiver to reconstruct the color of the original object. Further details of this process are found in GB 2,083,726A, the disclosure of which is hereby incorporated by reference.

Liquid crystal display devices are known for digital display in electronic calculators, clocks, household appliances, audio equipment, etc. Liquid crystal displays are being developed to replace cathode ray tube technology for display terminals. Liquid crystal displays occupy a smaller volume than cathode ray tube devices with the same screen area. In addition, liquid crystal display devices usually have lower power requirements than corresponding cathode ray tube devices.

There has been a need to incorporate a color display capability into such monochrome display devices, particularly in such applications as peripheral terminals using various kinds of equipment involving phototube display, mounted electronic display, or TV-image display. Various attempts have been made to incorporate a color display using a color filter array element into these devices. However, none of the color array elements for liquid crystal display devices so far proposed have been successful in meeting all the users' needs.

One commercially-available type of color filter array element which has been used in liquid crystal display devices for color display capability is a transparent support having a gelatin layer thereon which contains dyes having the additive primary colors red, green and blue in a mosaic pattern obtained by using a photolithographic technique. To prepare such a color filter array element, a gelatin layer is sensitized, exposed to a mask for one of the colors of the mosaic pattern, developed to harden the gelatin in the exposed areas, and washed to remove the unexposed (uncrosslinked) gelatin, thus producing a pattern of gelatin which is then dyed with dye of the desired color. The element is then recoated and the above steps are repeated to obtain the other two colors. Misalignment or improper deposition of color materials may occur during any of these operations. This method therefore contains many labor-intensive steps, requires careful alignment, is time-consuming and very costly. Further details of this process are disclosed in U.S. Pat. No. 4,081,277. U.S. Pat. No. 4,786,148 also discloses a color filter array element which employs certain pigments.

Color liquid crystal display devices generally include two spaced glass panels which define a sealed cavity which is filled with a liquid crystal material. For actively-driven devices, a transparent electrode is formed on one of the glass panels, which electrode may be patterned or not, while individually addressable electrodes are formed on the other of the glass panels. Each of the individual electrodes has a surface area corresponding to the area of one picture element or pixel. If the device is to have color capability, a color filter array with, e.g., red, green and blue color areas must be aligned with each pixel. Depending upon the image to be displayed, one or more of the pixel electrodes is energized during display operation to allow full light, no light or partial light to be transmitted through the color filter areas associated with that pixel. The image perceived by a user is a blending of colors formed by the transmission of light through adjacent color filter areas.

In forming such a liquid crystal display device, the color filter array element to be used therein may have to undergo rather severe heating and treatment steps during manufacture. For example, a transparent conducting layer, such as indium tin oxide (ITO), is usually vacuum sputtered onto the color filter array element which is then cured and patterned by etching. The curing may take place at temperatures elevated as high as 200° C. for times which may be as long as one hour or more. This is followed by coating with a thin polymeric alignment layer for the liquid crystals, such as a polyimide, followed by another curing step for up to several hours at an elevated temperature. These treatment steps can be very harmful to many color filter array elements, especially those with a gelatin matrix.

It is thus apparent that dyes used in color filter arrays for liquid crystal displays must have a high degree of heat and light stability above the requirements desired for dyes used in conventional thermal dye transfer imaging.

While a blue dye may be formed from a mixture of one or more magenta and one or more cyan dyes, not all such combinations will produce a dye mixture with the correct hue for a color filter array. Further, when a dye mixture with the correct hue is found, it may not have the requisite stability to heat and light. Also, hue shifts are less likely with a single dye and there is no need to balance the fade of the individual components of a mixture. It would be desirable to obtain a single blue dye of the correct hue rather than using a mixture of dyes.

U.S. Pat. No. 3,096,339 describes maleimide dyes useful in textile applications. Their use in thermal printing has not been disclosed.

It would be desirable to provide a color filter array element having high quality, good sharpness and which could be obtained easily and at a lower price than those of the prior art. It would also be desirable to provide such a color filter array element having a blue dye of the correct hue and which would have good stability to heat and light.

These and other objects are achieved in accordance with this invention which comprises a thermally-transferred color filter array element comprising a support having thereon a polymeric dye image-receiving layer containing a thermally-transferred image comprising a repeating pattern of a maleimide blue dye having the formula:

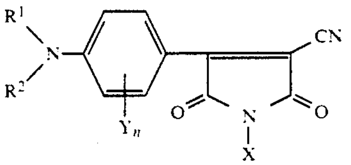

wherein:

$R^1$ and $R^2$ each independently represents hydrogen; a substituted or unsubstituted alkyl group having from 1 to about 8 carbon atoms such as methyl, ethyl, propyl, isopropyl, butyl, pentyl, hexyl, methoxyethyl, benzyl, 2-methane-sulfonylamidoethyl, 2-hydroxyethyl, 2-cyanoethyl, methoxycarbonylmethyl, etc.; a cycloalkyl group having from about 5 to about 8 carbon atoms, such as cyclohexyl, cyclopentyl, etc,; or a substituted or unsubstituted alkenyl group having from about 2 to about 8 carbon atoms, such as $CH_2CH{=}CH_2$, $CH_2CH{=}CHCH{=}CH_2$, $CH_2CH{=}CHCH_2OCH_3$, or $CH_2CH{=}CHC_5H_{11}$;

$R^1$ and $R^2$ may represent the elements which may be taken together to form a 5- or 6-membered heterocyclic ring, such as morpholine, pyrazole, pyrrolidone or piperazine;

each Y independently represents hydrogen; a substituted or unsubstituted alkyl group having from 1 to about 8 carbon atoms such as those listed above for $R^1$; an alkoxy group such as $OR^1$; halogen such as fluorine, chlorine or bromine; or two adjacent Y's may represent the atoms which may be taken together to form a fused carbocyclic aromatic ring such as naphthaline;

n is 0 to 4;

the position of Y ortho to the nitrogen may also be combined with $R^1$ to form a 5- or 6-membered non-aromatic, single or double nitrogen-containing, heterocyclic ring, thus forming a fused ring system such as tetrahydroquinoline, dihydroquinoline, indoline, etc.; and X is $R^1$, a substituted or unsubstituted acyl group having from 2 to about 9 carbon atoms such as

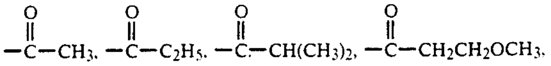

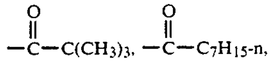

or

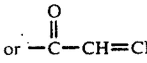

a substituted or unsubstituted aroyl group having from about 7 to about 18 carbon atoms, such as

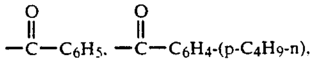

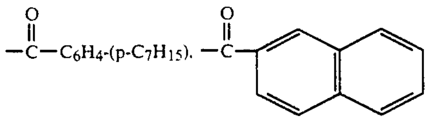

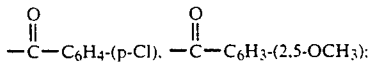

or a substituted or unsubstituted heteroaroyl group having from about 2 to about 10 carbon atoms, such as

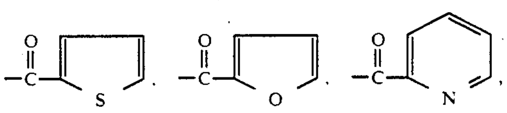

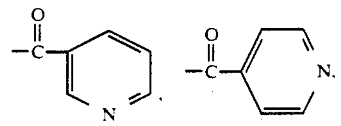

or

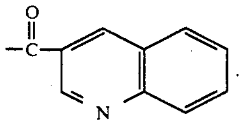

The dyes of the invention are selected to have a blue hue with a wavelength maximum between 580 and 620 nm.

In a preferred embodiment of the invention, the position of Y ortho to the nitrogen is combined with $R^1$ to form a 6-membered, nitrogen-containing, heterocyclic ring. In another preferred embodiment, Y is $OCH_3$ and X is $CH_2CH{=}CH_2$, $CH_2C_6H_5$ or $COC_6H_5$.

Specific blue dyes useful in the invention include the following:

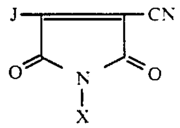
| DYE | J | X |
|---|---|---|
| 1 | 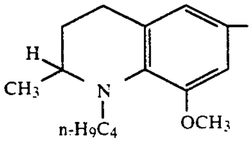 | $CH_2CH{=}CH_2$ |
| 2 | 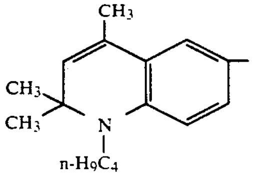 | $CH_2CH{=}CH_2$ |
| 3 | 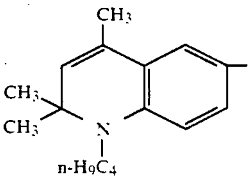 | $CH_2C_6H_5$ |
| 4 | 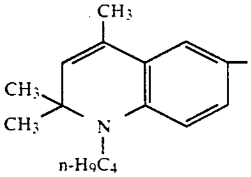 | $COC_6H_5$ |
| 5 | 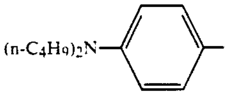 | 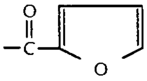 |
| 6 | 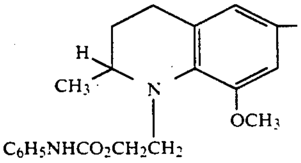 | $CH_2CH{=}CH_2$ |
| 7 | 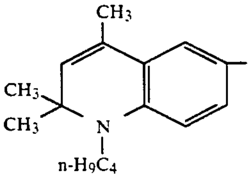 | $CH_2-C_6H_4$-p-Cl |
| 8 | 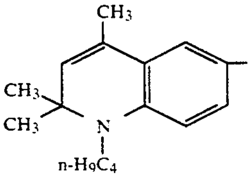 | $CH_2-C_6H_4$-p-$NO_2$ |

-continued
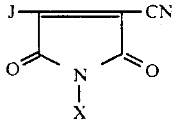
| DYE | J | X |
| --- | --- | --- |
| 9 | 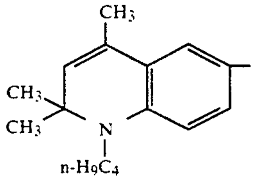 | $CH_2-C_6H_4$-p-$C(CH_3)_3$ |
| 10 | 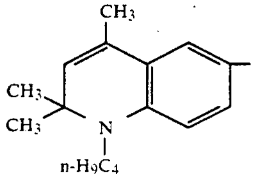 | $CH_2-C_6H_4$-p-F |
| 11 | 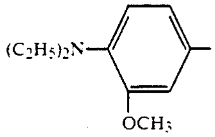 | $COC_6H_5$ |
| 12 | 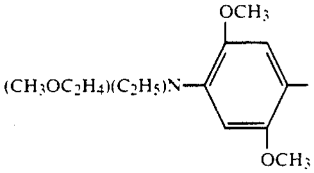 | $CH_2C_6H_5$ |
| 13 | 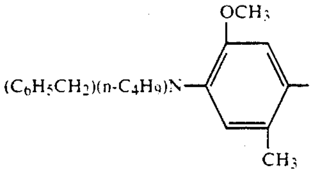 | $COC_2H_5$ |
| 14 | 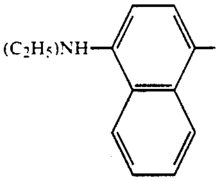 | $C_2H_5$ |
| 15 | 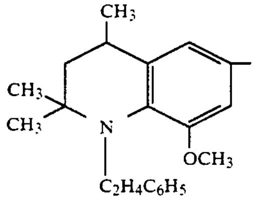 | 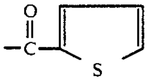 |
| 16 | 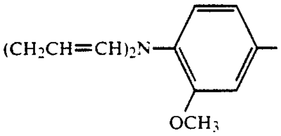 | $COC_6H_5$ |

-continued

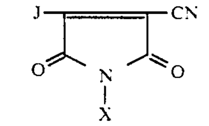

| DYE | J | X |
|---|---|---|
| 17 | 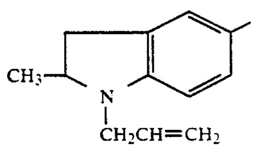 | $CH_2C_6H_5$ |
| 18 | 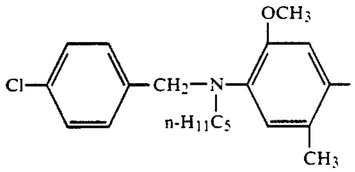 | $COC_6H_5$ |
| 19 | 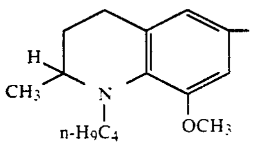 | $COC_6H_5$ |
| 20 | 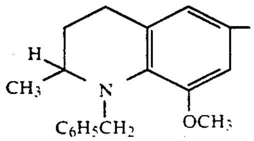 | $CH_2$—$C_6H_4$-p-Cl |

As noted above, the dye image-receiving layer contains a thermally-transferred image comprising a repeating pattern of colorants in the polymeric dye image-receiving layer, preferably a mosaic pattern.

In a preferred embodiment of the invention, the mosaic pattern consists of a set of red, green and blue additive primaries.

In another preferred embodiment of the invention, each area of primary color and each set of primary colors are separated from each other by an opaque area, e.g., black grid lines. This has been found to give improved color reproduction and reduce flare in the displayed image.

The size of the mosaic set is not critical since it depends on the viewing distance. In general, the individual pixels of the set are from about 50 to about 600 μm and do not have to be of the same size.

In a preferred embodiment of the invention, the repeating mosaic pattern of dye to form the color filter array element consists of uniform, square, linear repeating areas, with one color diagonal displacement as follows:

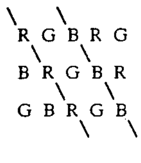

In another preferred embodiment, the above squares are approximately 100 μm.

The color filter array elements prepared according to the invention can be used in image sensors or in various electro-optical devices such as electroscopic light valves or liquid crystal display devices. Such liquid crystal display devices are described, for example, in UK Patents 2,154,355; 2,130,781; 2,162,674 and 2,161,971.

Liquid crystal display devices are commonly made by placing a material, which is liquid crystalline at the operating temperature of the device, between two transparent electrodes, usually indium tin oxide coated on a substrate such as glass, and exciting the device by applying a voltage across the electrodes. Alignment layers are provided over the transparent electrode layers on both substrates and are treated to orient the liquid crystal molecules in order to introduce a twist of, e.g., 90°, between the substrates. Thus, the plane of polarization of plane polarized light will be rotated in a 90° angle as it passes through the twisted liquid crystal composition from one surface of the cell to the other surface. Application of an electric field between the selected electrodes of the cell causes the twist of the liquid crystal composition to be temporarily removed in the portion of the cell between the selected electrodes. By use of optical polarizers on each side of the cell, polarized light can be passed through the cell or extinguished, depending on whether or not an electric field is applied.

The polymeric alignment layer described above may be any of the materials commonly used in the liquid crystal art. Such materials include polyimides, polyvinyl alcohol, methyl cellulose, etc.

The transparent conducting layer described above is also conventional in the liquid crystal art. Such materials include indium tin oxide, indium oxide, tin oxide, cadmium stannate, etc.

The dye image-receiving layer used in forming the color filter array element of the invention may comprise, for example, those polymers described in U.S. Pat. Nos. 4,695,286, 4,740,797, 4,775,657, and 4,962,081, the disclosures of which are hereby incorporated by reference. In a preferred embodiment, polycarbonates having a glass transition temperature greater than about 200° C. are employed. In another preferred embodiment, polycarbonates derived from a methylene substituted bisphenol-A are employed such as 4,4'-(hexahydro-4,7-methanoindan-5-ylidene)-bisphenol. In general, good results have been obtained at a coverage of from about 0.25 to about $5 mg/m^2$.

The support used in the invention is preferably glass such as borax glass, borosilicate glass, chromium glass, crown glass, flint glass, lime glass, potash glass, silica-flint glass, soda glass, and zinc-crown glass. In a preferred embodiment, borosilicate glass is employed.

Various methods may be used to transfer dye from the dye donor to the transparent support to form the color filter array element of the invention. There may be used, for example, a high intensity light flash technique with a dye-donor containing an energy absorptive material such as carbon black or a light-absorbing dye. Such a donor may be used in conjunction with a mirror which has a grid pattern formed by etching with a photoresist material. This method is described more fully in U.S. Pat. No. 4,923,860.

Another method of transferring dye from the dye donor to the transparent support to form the color filter array element of the invention is to use a heated embossed roller as described more fully in U.S. Pat. No. 4,978,652.

In another embodiment of the invention, the imagewise-heating is done by means of a laser using a dye-donor element comprising a support having thereon a dye layer and an absorbing material for the laser, the imagewise-heating being done in such a way as to produce a repeating mosaic pattern of colorants.

Any material that absorbs the laser energy or high intensity light flash described above may be used as the absorbing material such as carbon black or nonvolatile infrared-absorbing dyes or pigments which are well known to those skilled in the art. In a preferred embodiment, cyanine infrared absorbing dyes are employed as described in U.S. Pat. No. 4,973,572, the disclosure of which is hereby incorporated by reference.

After the dyes are transferred to the receiver, the image may be treated to further diffuse the dye into the dye-receiving layer in order to stabilize the image. This may be done by radiant heating, solvent vapor, or by contact with heated rollers. The fusing step aids in preventing fading and surface abrasion of the image upon exposure to light and also tends to prevent crystallization of the dyes. Solvent vapor fusing may also be used instead of thermal fusing.

A process of forming a color filter array element according to the invention comprises a) imagewise-heating a dye-donor element comprising a support having thereon a dye layer as described above, and b) transferring portions of the dye layer to a dye-receiving element comprising a support having thereon a dye-receiving layer, the imagewise-heating being done in such a way as to produce a repeating pattern of dyes to form the color filter array element.

A dye-donor element that is used to form the color filter array element of the invention comprises a support having thereon a blue dye as described above along with other colorants such as imaging dyes or pigments to form the red and green areas. Other imaging dyes can be used in such a layer provided they are transferable to the dye-receiving layer of the color array element of the invention by the action of heat. Especially good results have been obtained with sublimable dyes. Examples of additive sublimable dyes include anthraquinone dyes, e.g., Kayalon Polyol Brilliant Blue N BGM ® Kayalon Polyol Brilliant Blue N-BGM ® (Nippon Kayaku Co., Ltd.); azo dyes such as Kayalon Polyol Brilliant Blue BM ® and Kayalon Polyol Dark Blue 2BM ® (Nippon Kayaku Co., Ltd.); direct dyes such as Direct Dark Green B ® (Mitsubishi Chemical Industries, Ltd.); basic dyes such as Sumicacryl Blue 6G ® (Sumitomo Chemical Co., Ltd.), and Aizen Malachite Green ® (product of Hodogaya Chemical Co., Ltd.). Examples of subtractive dyes useful in the invention include the following:

(magenta)

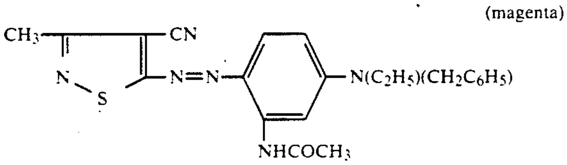

(yellow)

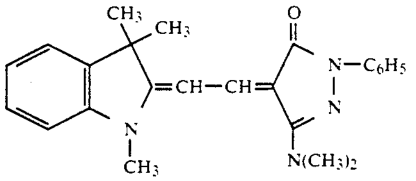

(cyan)

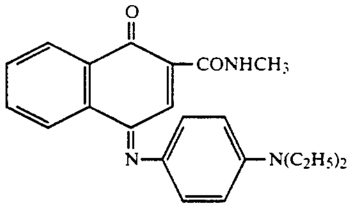

or any of the dyes disclosed in U.S. Pat. No. 4,541,830. The above cyan, magenta, and yellow subtractive dyes may be employed in various combinations, either in the dye-donor itself or by being sequentially transferred to the dye image-receiving element, to obtain the other desired green and red additive primary colors. The dyes may be mixed within the dye layer or transferred sequentially if coated in separate dye layers. The dyes may be used at a coverage of from about 0.05 to about $1 g/m^2$.

The imaging dye, and an infrared-absorbing material if one is present, are dispersed in the dye-donor element in a polymeric binder such as a cellulose derivative, e.g., cellulose acetate hydrogen phthalate, cellulose acetate. cellulose acetate propionate, cellulose acetate butyrate. cellulose triacetate; a polycarbonate; poly(styrene-co-acrylonitrile), a poly(sulfone) or a poly(phenylene oxide). The binder may be used at a coverage of from about 0.1 to about 5 $g/m^2$.

The dye layer of the dye-donor element may be coated on the support or printed thereon by a printing technique such as a gravure process.

Any material can be used as the support for the dye-donor element provided it is dimensionally stable and can withstand the heat generated by the thermal transfer device such as a laser beam. Such materials include polyesters such as poly(ethylene terephthalate); polyamides; polycarbonates; glassine paper; condenser paper; cellulose esters; fluorine polymers; polyethers; polyacetals; polyolefins; and polyimides. The support generally has a thickness of from about 2 to about 250 μm. It may also be coated with a subbing layer, if desired.

Several different kinds of lasers could conceivably be used to effect the thermal transfer of dye from a donor sheet to the dye-receiving element to form the color filter array element in a preferred embodiment of the invention, such as ion gas lasers like argon and krypton; metal vapor lasers such as copper, gold, and cadmium; solid state lasers such as ruby or YAG; or diode lasers such as gallium arsenide emitting in the infrared region from 750 to 870 nm. However, in practice, the diode lasers offer substantial advantages in terms of their small size, low cost, stability, reliability, ruggedness, and ease of modulation. In practice, before any laser can be used to heat a dye-donor element, the laser radiation must be absorbed into the dye layer and converted to heat by a molecular process known as internal conversion. Thus, the construction of a useful dye layer will depend not only on the hue, sublimability and intensity of the image dye, but also on the ability of the dye layer to absorb the radiation and convert it to heat.

Lasers which can be used to transfer dye from the dye-donor element to the dye image-receiving element to form the color filter array element in a preferred embodiment of the invention are available commercially. There can be employed, for example, Laser Model SDL-2420-H2® from Spectrodiode Labs, or Laser Model SLD 304 V/W® from Sony Corp.

The following example is provided to illustrate the invention.

EXAMPLE

A blue dye-donor was prepared by coating on a gelatin subbed transparent 175 μm poly(ethylene terephthalate) support a dye layer containing the blue dyes illustrated above and identified in Table 1 below in a cellulose acetate propionate (2.5% acetyl, 46% propionyl) binder (0.27 $g/m^2$) coated from a 1-propanol, butanone, toluene and cyclopentanone solvent mixture. The dye layer also contained Regal 300® (Cabot Co.) (0.22 $g/m^2$) ball-milled to submicron particle size, Fluorad FC-431® dispersing agent (3M Company) (0.01 $g/m^2$) and Solsperse® 24000 dispersing agent (ICI Corp.) (0.03 $g/m^2$). A dye-donor containing a mixture of dyes 1 and 2 was also prepared as described above.

Control dye-donors were prepared as described above but using the control dyes identified below. For both the invention and control dye-donors, the quantity of dye coated in the dye-donor was varied to give approximately equal transferred densities.

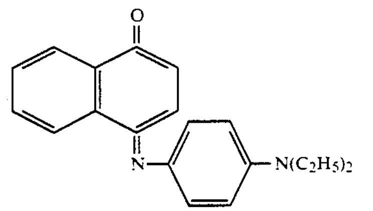
C-1

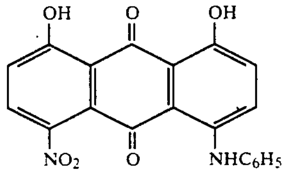
C-2

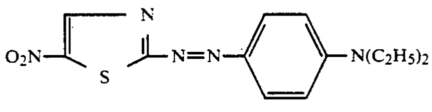
C-3

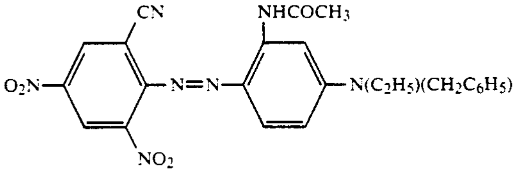
C-4

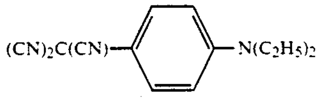
C-5

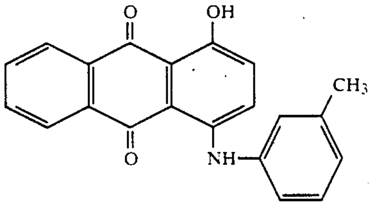
C-6

C-7: a mixture of the following magenta and cyan dyes to produce a blue hue:

(magenta)

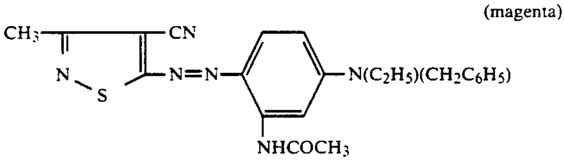

(cyan)

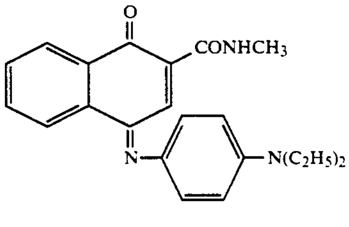

C-8: a mixture of the following magenta and cyan dyes to produce a blue hue;

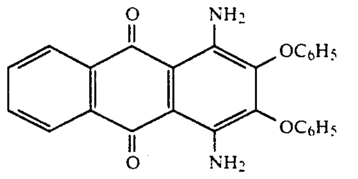

(magenta)

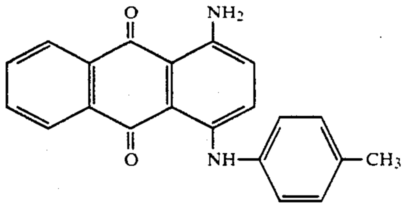

(cyan)

C-9: a mixture of the cyan dye of C-7 and the dye of C-5.

A dye-receiver was prepared by spin-coating the following layers on a 1.1 mm thick flat-surfaced borosilicate glass:

1) Subbing layer of VM-651 Adhesion Promoter (duPont) as a 1% solution in a methanol-water solvent mixture (0.5 μm thick layer equivalent to 0.54 g/$m^2$), and 2) Receiver layer of a polycarbonate of 4,4'-(hexahydro-4,7-methanoindene-5-ylidene)bisphenol (2.5 g/m2), as described in U.S. Pat. No. 4,962,081, from methylene chloride solvent.

After coating, the receiver plate was heated in an oven at 60° C. for one hour to remove residual solvent.

Each dye-donor was placed face down upon the dye-receiver. A Mecablitz® Model 402 (Metz AG Company) electronic flash unit was used as a thermal energy source. It was placed 40 mm above the dye-donor using a 45-degree mirror box to concentrate the energy from the flash unit to a 25×50 mm area. The dye transfer area was masked to 12×25 mm. The flash unit was flashed once to produce a transferred Status A transmission density of between 1.0 and 3.0.

Each transferred test sample was placed in a sealed chamber saturated with acetone vapors for 5 minutes at 20° C. to diffuse the dyes into the receiver layer. The transferred dye images were then placed under a Pyropanel No. 4083 infrared heat panel at 200° C. for 60 sec. to remove residual solvent.

The Status A Red, Green and Blue transmission densities of the transferred images were read. For a dye to be successfully used as a blue filter dye in a color filter array, it is highly desirable that the dye be both thermally stable and capable of absorbing a maximum of green and red light (blue hue) while at the same time transmitting a minimum of blue light, i.e., having minimal absorption in the blue light region. To evaluate this for comparative purposes, the ratio of the red to blue and ratio of the green to blue densities were calculated. A high value for each is desired.

The thermal stability of the dyes were evaluated by heating a transferred image for 2 hours at 180° C., and rereading the Status A red and green density, and calculating the percent density loss.

The following results were obtained:

TABLE 1

| Dye Donor | | Status A Transferred Density | | | | |
|---|---|---|---|---|---|---|
| Blue Dye (g/$m^2$) | Wavelength Maximum (nm) | R | G | B | R/B | G/B |
| C-1 (control) (0.63 | nd | 1.9 | 1.7 | 0.23 | 8 | 7 |
| C-2 (control) (1.20 | nd | 1.9 | 1.1 | 0.54 | 3 | 2 |
| C-3 (control) (0.22 | nd | 1.0 | 1.5 | 0.21 | 5 | 7 |
| C-4 (control) (0.22 | nd | 1.6 | 1.7 | 0.40 | 4 | 4 |
| C-5 (control) (0.18 | nd | <0.1 | 2.5 | 0.44 | <1 | 6 |
| C-6 (control) (1.02 | nd | 1.4 | 1.8 | 0.31 | 4 | 6 |
| C-7 (control) (0.48 + 0.25) | nd | 2.4 | 1.9 | 0.39 | 6 | 5 |
| C-8 (control) (0.72 + 0.93) | nd | 1.9 | 2.2 | 0.42 | 4 | 5 |
| C-9 (control) (0.48 + 0.18) | nd | 2.2 | 1.9 | 0.37 | 6 | 6 |
| 1 (0.48) | 580 | 1.8 | 1.9 | 0.15 | 12 | 12 |
| 2 (0.47) | 569 | 1.1 | 2.3 | 0.18 | 6 | 13 |
| 3 (0.51) | 572 | 1.0 | 1.7 | 0.13 | 8 | 13 |
| 4 (0.51) | 580 | 1.4 | 1.2 | 0.11 | 13 | 11 |
| 5 (0.40) | 552 | 0.4 | 2.1 | 0.17 | 2 | 12 |
| 6 (0.75) | 566 | 1.0 | 1.5 | 0.16 | 6 | 9 |
| 7 (0.55) | 574 | 1.1 | 1.5 | 0.11 | 10 | 13 |
| 8 (1.00) | 575 | 1.4 | 1.5 | 0.14 | 10 | 11 |
| 9 (0.60) | 573 | 0.9 | 1.5 | 0.12 | 7 | 13 |
| 10 (0.51) | 574 | 1.2 | 1.8 | 0.13 | 9 | 14 |
| 11 (0.25 + 0.24) | nd | 1.4 | 1.9 | 0.14 | 10 | 14 |

*Dye mixtures
nd = not determined

The above data indicate that the dyes of the invention transfer efficiently (high red and green maximum density) and have desirable spectral characteristics, high value for R/B and G/B transmission density. The wavelength maximum of each dye is also given.

TABLE 2

| | Density Loss (%) | |
|---|---|---|
| Dye-Donor | Red | Green |
| C-1 | 19 | 16 |
| C-2 | 2 | <2 |
| C-3 | 33 | 23 |
| C-4 | 5 | 4 |
| C-5 | 25 | 24 |
| C-6 | 15 | 18 |
| C-7 | 48 | 7 |
| C-8 | 29 | 6 |
| C-9 | 50 | 28 |
| 1 | 13 | 13 |
| 2 | 6 | 4 |
| 3 | 8 | <2 |
| 4 | 13 | <2 |
| 5 | 9 | 5 |
| 6 | 13 | 11 |
| 7 | 13 | 3 |
| 8 | 11 | 4 |
| 9 | 13 | <2 |
| 10 | 13 | 4 |
| 11 | 5 | 6 |

The above data indicate that the dyes of the invention show less density loss than all except two prior art control dyes.

The invention has been described in detail with particular reference to preferred embodiments thereof, but it will be understood that variations and modifications can be effected within the spirit and scope of the invention.

What is claimed is:

1. A thermally-transferred color filter array element comprising a support having thereon a polymeric dye image-receiving layer containing a thermally-transferred image comprising a repeating pattern of a maleimide blue dye having the formula:

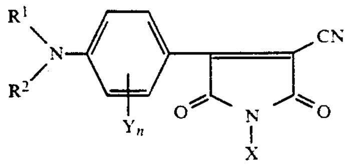

wherein:

$R^1$ and $R^2$ each independently represents hydrogen; a substituted or unsubstituted alkyl group having from 1 to about 8 carbon atoms; a cycloalkyl group having from about 5 to about 8 carbon atoms; or a substituted or unsubstituted alkenyl group having from about 2 to about 8 carbon atoms;

$R^1$ and $R^2$ may represent the elements which may be taken together to form a 5- or 6-membered heterocyclic ring;

each Y independently represents hydrogen; a substituted or unsubstituted alkyl group having from 1 to about 8 carbon atoms; an alkoxy group $OR^1$; halogen; or two adjacent Y's may represent the atoms which may be taken together to form a fused aromatic ring;

n is 0 to 4;

the position of Y ortho to the nitrogen may also be combined with $R^1$ to form a 5- or 6-membered non-aromatic, single or double nitrogen-containing, heterocyclic ring, thus forming a fused ring system; and X is $R^1$; a substituted or unsubstituted acyl group having from 2 to about 9 carbon atoms; a substituted or unsubstituted aroyl group having from about 7 to about 18 carbon atoms; or a substituted or unsubstituted heteroaroyl group having from about 2 to about 10 carbon atoms.

2. The element of claim 1 wherein said receiving layer comprises a polycarbonate binder having a glass transition temperature greater than about 200° C.

3. The element of claim 2 wherein said polycarbonate is derived from 4,4'-(hexahydro-4,7-methanoindene-5-ylidene)bisphenol.

4. The element of claim 1 wherein the position of Y ortho to the nitrogen is combined with $R^1$ to form a 6-membered, nitrogen-containing, heterocyclic ring.

5. The element of claim 1 wherein Y is $OCH_3$ and X is $CH_2CH{=}CH_2$, $CH_2C_6H_5$ or $COC_6H_5$.

6. The element of claim 1 wherein said pattern is a mosaic pattern of a set of red, green and blue additive primaries.

7. The element of claim 7 wherein said primary colors are separated from each other by an opaque area.

8. The element of claim 1 wherein said thermally-transferred image is obtained using laser induction.

9. The element of claim 1 wherein said thermally transferred image is obtained using a high intensity light flash.

10. The element of claim 1 wherein said support is glass.

11. A process of forming a color filter array element comprising:

a) imagewise-heating a dye-donor element comprising a support having thereon a dye layer, and b) transferring portions of said dye layer to a dye-receiving element comprising a support having thereon a dye-receiving layer, said imagewise-heating being done in such a way as to produce a repeating pattern of colorants, one of the colorants being a maleimide blue dye having the formula:

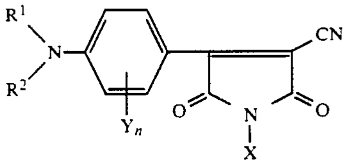

wherein:

$R^1$ and $R^2$ each independently represents hydrogen; a substituted or unsubstituted alkyl group having from 1 to about 8 carbon atoms; a cycloalkyl group having from about 5 to about 8 carbon atoms; or a substituted or unsubstituted alkenyl group having from about 2 to about 8 carbon atoms;

$R^1$ and $R^2$ may represent the elements which may be taken together to form a 5- or 6-membered heterocyclic ring;

each Y independently represents hydrogen; a substituted or unsubstituted alkyl group having from 1 to about 8 carbon atoms; an alkoxy group $OR^1$; halogen; or two adjacent Y's may represent the atoms which may be taken together to form a fused aromatic ring;

n is 0 to 4;

the position of Y ortho to the nitrogen may also be combined with $R^1$ to form a 5- or 6-membered non-aromatic, single or double nitrogen-containing, heterocyclic ring, thus forming a fused ring system; and X is $R^1$; a substituted or unsubstituted acyl group having from 2 to about 9 carbon atoms; a substituted or unsubstituted aroyl group having from about 7 to about 18 carbon atoms; or a substituted or unsubstituted heteroaroyl group having from about 2 to about 10 carbon atoms.

12. The process of claim 11 wherein said receiving layer comprises a a polycarbonate binder having a glass transition temperature greater than about 200° C.

13. The process of claim 11 wherein said polycarbonate is derived from 4,4'-(hexahydro-4,7-methanoindene-5-ylidene)bisphenol.

14. The process of claim 11 wherein the position of Y ortho to the nitrogen is combined with $R^1$ to form a 6-membered, nitrogen-containing, heterocyclic ring.

15. The process of claim 11 wherein Y is $OCH_3$ and X is $CH_2CH{=}CH_2$, $CH_2C_6H_5$ or $COC_6H_5$.

16. The process of claim 11 wherein said dye-donor element contains an additional light-absorbing material.

17. The process of claim 16 wherein a laser is used to supply energy in said imagewise-heating step.

18. The process of claim 16 wherein a high intensity light flash is used to supply energy in said imagewise-heating step.

19. The process of claim 11 which includes a further step of heating the transferred image to further diffuse the dye into said dye-receiving layer.

20. The process of claim 11 which includes a further step of subjecting the transferred image to solvent vapor to further diffuse the dye into said dye-receiving layer.

* * * * *